United States Patent
Allen et al.

(10) Patent No.: US 6,767,546 B1
(45) Date of Patent: Jul. 27, 2004

(54) USE OF ECHINACEA AS A FEED ADDITIVE TO ENHANCE PROTECTION AGAINST COCCIDIOSIS

(75) Inventors: Patricia C. Allen, Beltsville, MD (US); Mark Anderson, Chester, NY (US); Harry D. Danforth, Severn, MD (US)

(73) Assignees: The United States of America as represented by the Secretary of Agriculture, Washington, DC (US); Triarco Industries, Inc., Wayne, NJ (US)

( * ) Notice: Subject to any disclaimer, the term of this patent is extended or adjusted under 35 U.S.C. 154(b) by 0 days.

(21) Appl. No.: 09/931,033

(22) Filed: Aug. 17, 2001

(51) Int. Cl.[7] .......................... A61K 35/78; A23K 1/16; A23K 1/165; A23D 9/007; A01N 33/12
(52) U.S. Cl. ................................ 424/271.1; 424/267.1; 424/184.1; 426/635; 426/644; 426/652; 426/638; 426/640
(58) Field of Search ............................... 424/737, 271.1, 424/742, 267.1, 745, 746, 738, 265.1; 514/52, 643, 644, 642, 54; 426/401, 132, 611, 652, 601, 638, 607, 640, 635

(56) References Cited

U.S. PATENT DOCUMENTS

| | | | |
|---|---|---|---|
| 4,544,548 A | * 10/1985 | Davis et al. ................... | 424/93 |
| 5,122,471 A | 6/1992 | Jenkins et al. | |
| 5,311,841 A | * 5/1994 | Thaxton ...................... | 604/51 |
| 5,656,485 A | 8/1997 | Jacobson et al. | |
| 5,709,862 A | 1/1998 | Anderson et al. | |
| 5,770,217 A | * 6/1998 | Kutilek, III et al. ......... | 424/442 |
| 5,891,465 A | * 4/1999 | Keller et al. ................. | 424/450 |
| 6,149,912 A | 11/2000 | Gubarev et al. | |
| 6,203,801 B1 | 3/2001 | Schaap et al. | |
| 6,312,746 B2 | * 11/2001 | Paluch ........................ | 425/282 |
| 6,355,684 B1 | * 3/2002 | Squires ....................... | 514/643 |

OTHER PUBLICATIONS

Rehman, J et al, Immunology Letters, vol. 68(2–3), pp. 391–395, Jun. 1, 1999, (abstract only).*

Hochertz, S, Arzneimittel–Forschung, Sep. 1990, vol. 40(9), pp. 1068–1072, (English abstract).*

Schranner, I et al, Zentralblatt fur Veterinarmedizin, Series B, Jul. 1989, vol. 36(5), pp. 353–364, English abstract.*

Vukovic, Laurel, Natural Health, vol. 27, No. 5, p. 121 (25), Sep.–Oct. 1998.*

Danforth, H.D., "Use of Live Oocyst Vaccines in the Control of Avian Coccidiosis: Experimental Studies and Field Trials", *International J. of Parasitology*, vol. 28, pp. 1099–1109, 1998.

Steinmuller, C., et al., "Polysaccharides Isolated From Plant Cell Cultures of Echinacea Purpurea Enhance the Resistance of Immunosuppressed Mice Against Systemic Infections with Candida Albicans and Listeria Monocytogenes", *Int. J. Immunopharmac.*, vol. 15, (5), pp. 605–614, 1993.

Roesler, J., et al., "Application of Purified Polysaccharides from Cell Cultures of the Plant Echinacea Purpurea to Test Subjects Mediates Activation of the Phagocyte System", *Int. J. Immunopharmac.*, vol. 13, (7), pp. 931–941, 1991.

Roesler, J., et al., "Application of Purified Polysaccharides from Cell Cultures of the Plant Echinacea Purpurea to Mice Mediates Protection Against Systemic Infections with Listeria Monocytogenes and Candida Albicans", *Int. J. Immunopharmac.*, vol. 13, (1), pp. 27–37, 1991.

Stimpel, M., et al., "Macrophage Activation and Induction of Macrophage Cytotoxicity by Purified Polysaccharide Fractions from the Plant *Echinacea purpurea*", Infection and Immunity, vol. 46, (3), pp. 845–849, Dec. 1984.

* cited by examiner

*Primary Examiner*—Lynette R. F. Smith
*Assistant Examiner*—Ginny Allen Portner
(74) *Attorney, Agent, or Firm*—John D. Fado; G. Byron Stover

(57) ABSTRACT

Echinacea dietary supplements are useful adjuvants for live anticoccidial vaccines. Feed supplementation with Echinacea preparations enhances the immune response to such vaccines. *Echinacea purpurea* in amounts of about 0.1% to 0.5% administered for about two weeks to day-old chicks has been found effective for providing significant weight gain compared to vaccination alone.

6 Claims, 6 Drawing Sheets

USE OF ECHINACEA AS A FEED ADDITIVE TO ENHANCE PROTECTION AGAINST COCCIDIOSIS

BACKGROUND OF THE INVENTION

1. Field of the Invention

Anticoccidial drugs have been used for the prevention of coccidiosis in poultry for many years. Although these programs have generally been considered effective, the development of resistance by avian coccidia to the drugs in current use has resulted in continued losses by the poultry industry to the disease. There is thus a strong incentive to develop more effective anticoccidia products and processes that will provide better protection against challenge by virulent field strains. This invention relates to preparations of the plant *Echinacea purpurea* which serve as novel dietary supplements for enhancing the effectiveness of vaccines against coccidia species and to methods utilizing these preparations in vaccination protocols.

2. Description of the Related Art

Coccidiosis in poultry is a disease resulting from infection by avian coccidia. These microorganisms are parasitic protozoa, and those belonging to the genus Eimeria are economically the most important and include *E. acervulina, E. mivati, E. mitis, E. praecox, E. hagani, E. necatrix, E. maxima, E. brunetti* and *E. tenella*. *Eimeria tenella* is the most pathogenic of the group and has thus received the most attention.

Although coccidiosis occurs in both invertebrates and vertebrates, including man, the poultry industry has been particularly affected by the disease, with coccidiosis being the most economically important parasitic disease of chickens. Problems associated with the disease are varied and range from poor feed conversion and reduced weight gain and egg production in light infections to morbidity and mortality in heavier infections. The parasite has an asexual/sexual life cycle which occurs in the intestinal tract of an infected bird. Infection occurs when birds ingest sporulated oocysts which are generally associated with fecal material. During the digestive process, the oocysts rupture, releasing asexual sporozoites into the digestive tract. Sporozoites subsequently invade epithelial cells of the intestinal tract where they eventually mature and release merozoites back into the digestive tract. Merozoites differentiate into gametocytes, thus initiating the sexual stage of the coccidia life cycle. The gametocytes fuse to produce the fertilization product, oocysts, which are released into the feces, or droppings, of infected birds. The formation of oocysts completes the life cycle of the parasite. Sporulation within the oocyst may then occur followed by transmission of the disease through ingestion by a new host. Characteristic digestive tract lesions are produced by the developing asexual and sexual stages.

Prevention or treatment of the disease by administration of anticoccidial agents such as ionophore drugs has generally been successful in the past, however, the development of drug-resistant strains has presented new challenges. A number of vaccines have been developed, including both live (virulent and attenuated), antigenic components and various recombinants. Schaap et al. (U.S. Pat. No. 6,203, 801, Mar. 20, 2001) disclosed a 25-kd Eimeria polypeptide which may be used as an immunogen. Danforth, H. D. (1998. *J. Parasitol.* vol. 28, pp. 1099–1109) disclosed live oocyst vaccines using a virulent field strain isolate of *E. maxima*, while Danforth et al. (1997. *Parasitol. Res.* vol. 83, pp. 445–451) described evaluations of a four-species (*E. acervulina, E. maxima, E. necatrix* and *E. tenella*) virulent oocyst vaccine. Anderson et al. (U.S. Pat. No. 5,709,862, Jan. 20, 1998) disclosed recombinant antigenic peptides containing a determinant or determinants for use as vaccines.

*Echinacea purpurea* has been known for more than a century as a medicinal herb, and extracts from the plant have been implicated in immune-type responses. Purified polysaccharide fractions from Echinacea were reported to activate macrophages (Stimpel et al. 1984. *Infect. Immun.* vol. 46, pp. 845–849), to mediate action of the phagocyte system (Roesler et al. 1991. *Int. J. Immunopharmac.* vol. 13, pp. 27–37 and 931–941) and to protect against systemic infections in immunosuppressed mice (Steinmüller et al. 1993. *Int. J. Immunopharmac.* vol. 15, pp. 605–614). These studies were all carried out in mammalian (either human or mouse) systems, however, and there are no reports of effects on avian systems.

Although vaccine development represents significant progress in controlling coccidiosis, the disease continues to present problems for the poultry industry and results in considerable economic loss. There is thus a need to provide products and processes which are capable of improving resistance to the disease.

SUMMARY OF THE INVENTION

We have discovered that ingestion of preparations of Echinacea along with immunization provides significant advantage over immunization alone. In accordance with this discovery, it is an object of the invention to provide a method of treating birds to provide resistance to coccidiosis by the administration of both Echinacea and a vaccine to the birds.

It is also an object of the invention to provide a composition comprising Echinacea in amounts effective for providing resistance to coccidiosis when ingested in combination with immunization.

Other objects and advantages of the invention will become readily apparent from the following description.

DETAILED DESCRIPTION OF THE INVENTION

Figure 1:
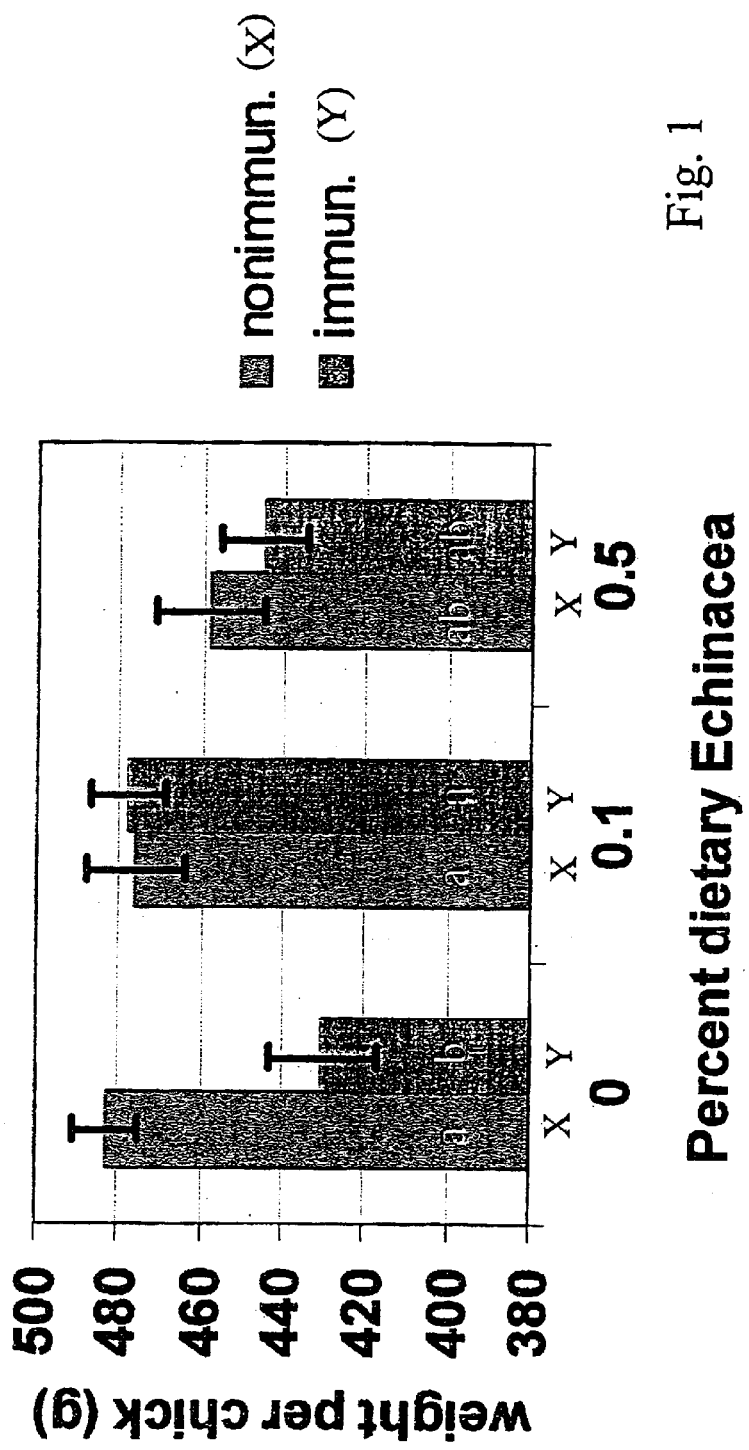
FIG. 1 shows the interactive effects of immunization and dietary Echinacea on body weight of chicks at 2 weeks of age. $^{ab}$Values are means±SEM. Columns with no common letter have significantly different values (p>0.05).

Coccidiosis in chickens is an intestinal infection caused by several species of Eimeria. Conditions associated with the disease include nutrient malabsorption, reduced weight gain, morbidity and mortality. The primary treatment protocols for the disease have conventionally relied upon anticoccidial drugs, however, the development of resistance to these drugs (Stephen et al. 1997. Vet. Parasitol. vol. 69, pp. 19–29) has led to a search for alternative treatments. The commercial use of live vaccines has thus increased (Danforth, H. D., supra), however the success of these vaccines has been somewhat limited. The vaccines act by allowing a buildup of immunity over time as a result of the recycling of the parasites over several life cycles. Vaccine performance has been inconsistent under these conditions, leading to efforts to develop protocols which would improve consistency as well as effectiveness.

The novel process of the invention provides effective protection for poultry against infection by coccidia species. Although the method and composition are effective for any poultry species susceptible to infection, for convenience, the discussion will be limited to the treatment of chickens. The method involves two steps: one, an Echinacea preparation is added to the dietary regimen of the birds, and two, the birds are immunized with an effective anticoccidial vaccine. Preferably, the two steps are carried out simultaneously, and administration is begun on 1-day-old birds. The Echinacea preparation is added to the dietary composition in an amount which is effective for enhancing the immune response to the anticoccidial vaccine. An effective amount is at least about 0.1% (w/w) and up to about 0.5% (w/w). A wide range of poultry feeds are commercially available which are useful in the novel composition and may be selected according to age and type of poultry being fed. Since it is preferable to begin treatment at as early an age as possible, a diet suitable for young birds is recommended. Examples of useful poultry feeds include broiler starter mash (4050, Southern States, Richmond, Va.). Typically, effective poultry feed used as starter feed for young chicks provides about 24% crude protein, about 4% crude fiber, about 5% crude fat and about 6800 kcal/kg (poultry metabolizable energy). As the birds mature, the basic diet may be adjusted accordingly. The minimum time for providing Echinacea-containing composition as the dietary regimen is about 2 weeks. The birds should be removed from Echinacea supplementation at any time after the initial two-week period.

Echinacea preparations are well-known since they have been utilized as herbal supplements in mammalian diets for many years. Powders ground from both the herb and root portions of the plants as well as aqueous alcohol extracts from either portion may be utilized. Effective Echinacea products which are commercially available are FingerPrint® Botanicals (Triarco Industries, Paterson, N.J.). The major components and characteristics of these products are presented in Table 1.

TABLE 1

Description of Echinacea Products Useful as Dietary Supplements.

| Botanical name | Echinacea purpurea | |
| --- | --- | --- |
| Part used | Whole root | Herb |
| Appearance | Powder | Powder |
| Mesh size | 60, 80 | 60, 80 |
| Bulk density (g/mL) | 0.36 | 0.32 |
| Constituents | | |
| chicoric acid | 2.3% | 2.88% |
| polysaccharides | 0.01–10% | 0.01–10% |
| isobutylamides | 0.001–10% | 0.001–10% |
| polyphenols | — | 3.12% |

The vaccine utilized may be any which is effective against coccidial parasites, and administration of the vaccine should be carried out as appropriate for the particular vaccine selected. A vaccine is defined herein as any type of biological agent in an administratable form capable of stimulating an immune response in an animal inoculated with the vaccine. An effective vaccine which is commercially available is Immucox® (Vetech Laboratories, Ltd., Rockwood, Ontario, Canada), a live vaccine comprised of a mixture of live oocysts of E. acervulina, E. tenella, E. maxima and E. necatrix.

The effects of dietary supplementation with 0.1% and 0.5% E. purpurea on the development of immunity following live vaccination and subsequent challenge with multiple species was examined. Since one of the manifestations of coccidiosis is reduced weight gain, the effects of immunization and diet on weight gains before challenge, and weight gains, lesion scores and plasma levels of carotenoids and $NO_2^- + NO_3^-$ following challenge were determined.

Experiments were carried out as described in the Example. Day-old chicks were placed on one of three diets: normal ration supplemented with 0, 0.1% or 0.5% E. purpurea. Half of each diet group was immunized orally with Immucox® (at half strength), resulting in six treatment groups. At two weeks, all chickens were placed on an unsupplemented diet for a further two weeks. At that time, the six treatment groups were each divided into a challenged or unchallenged group of equal mean weight. Chicks in challenged groups were each given a 1000× oral dose of the live vaccine. At six days post challenge, chickens were weighed, bled, killed and scored for lesions in upper and middle small intestine and ceca. Plasma samples were analyzed for carotenoids and nitrite/nitrate levels.

Figure 2:
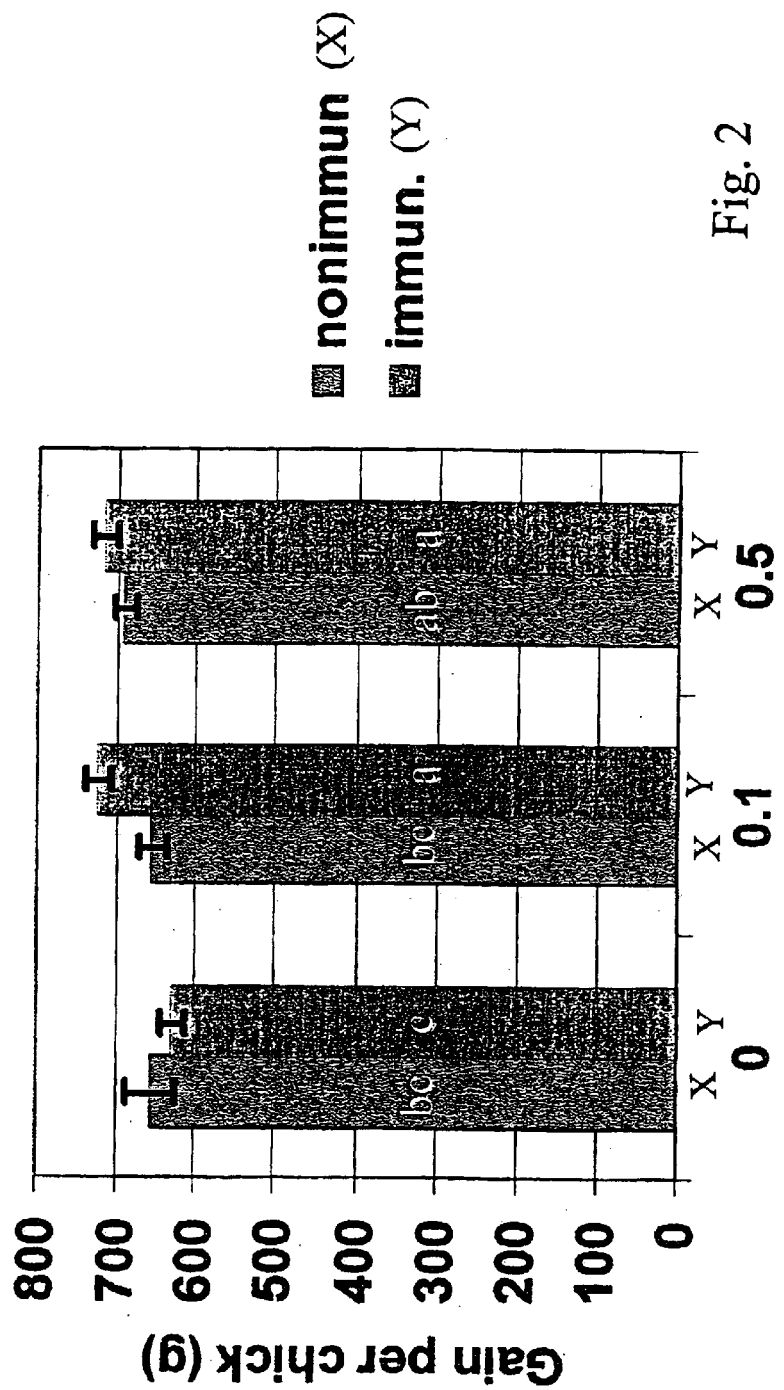
FIG. 2 shows the growth of chicks on nonsupplemented feeding regimen for a 2-week period subsequent to the supplemented regimen. $^{abc}$Values are means±SEM. Columns with no common letter have significantly different values (p>0.05).
Figure 3:
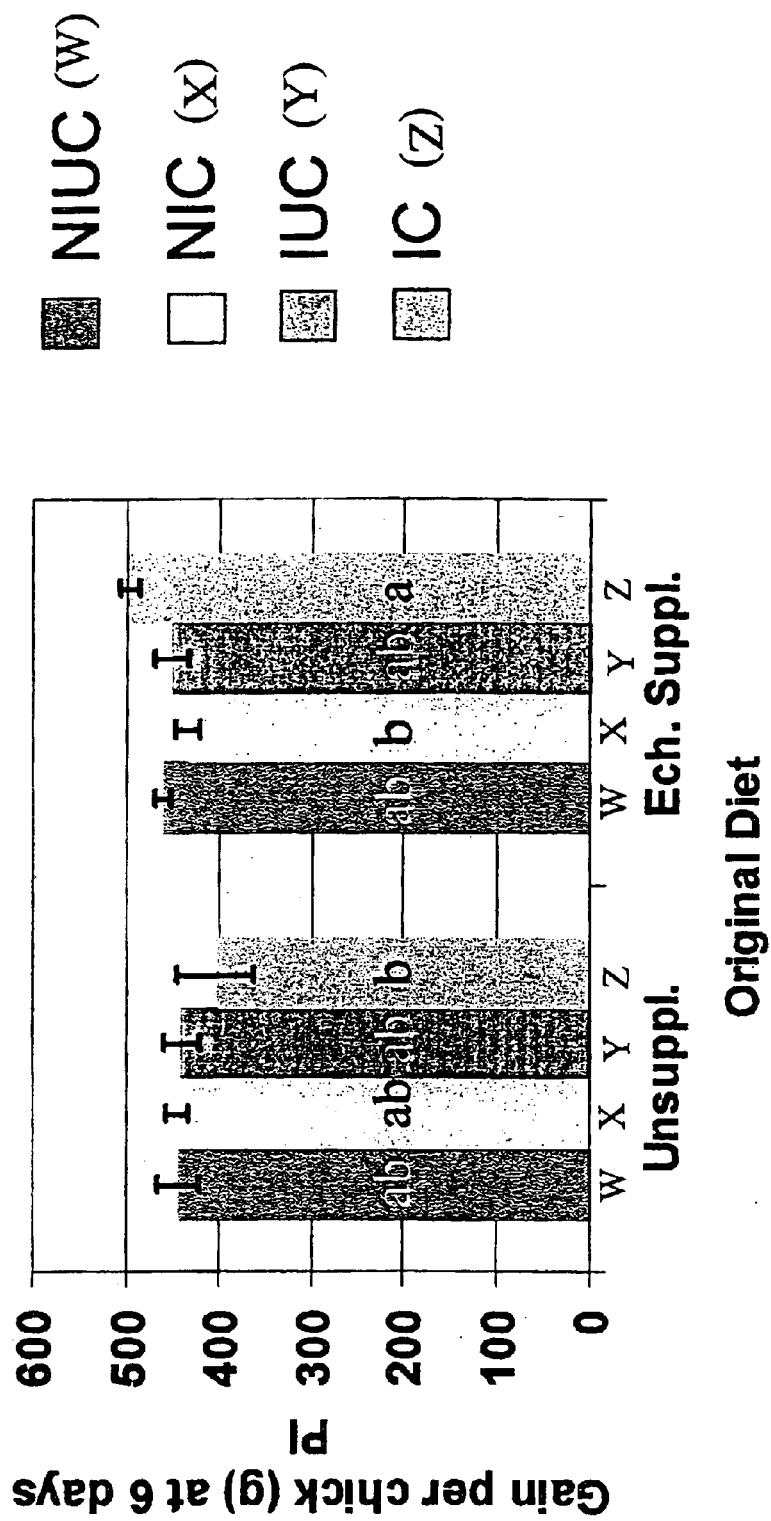
FIG. 3 shows the effect of challenge with coccidia on weight gain at 6 days post inoculation (PI). NIUC= nonimmunized, unchallenged; NIC=nonimmunized, challenged; IUC=immunized, unchallenged; IC=immunized, challenged. $^{ab}$Values are means±SEM. Columns with no common letter have significantly different values (p>0.05).

At two weeks, immunization significantly depressed weight gains (436±13 g) of chicks on unsupplemented diet compared to unimmunized chicks (483±8 g). Supplementation of the diet with 0.1% or 0.5% Echinacea resulted in gains that were not significantly different from unimmunized controls (FIG. 1). During the subsequent two weeks on unsupplemented diet, chickens that had been immunized and that had consumed either level of Echinacea gained significantly more (720±16 g) than those consuming unsupplemented diet only (673±15 g) (FIG. 2). At six days post challenge (FIGS. 3 and 4), no significant difference due to diet level of Echinacea was observed within each of the six immunization/challenge treatment groups, so data from the 0.1% and 0.5% levels were combined. Chicks that were immunized and that had consumed Echinacea supplements gained significantly more (495±10 g) than immunized chicks with no Echinacea supplement (403±41 g) or unimmunized chicks with Echinacea supplement (434±12 g). Immunized, Echinacea-fed chicks had significantly lower total lesion scores (0.9±0.2) compared to immunized, unsupplemented (2.5±0.3) or unimmunized, unsupplemented (3.9±0.3) or supplemented (3.6±0.2) (Table 2). Challenge infection significantly lowered

TABLE 2

Lesion scores in chicks on Echinacea-supplemented and -unsupplemented diets, and immunized and unimmunized with anticoccidial vaccine.

Figure 4:
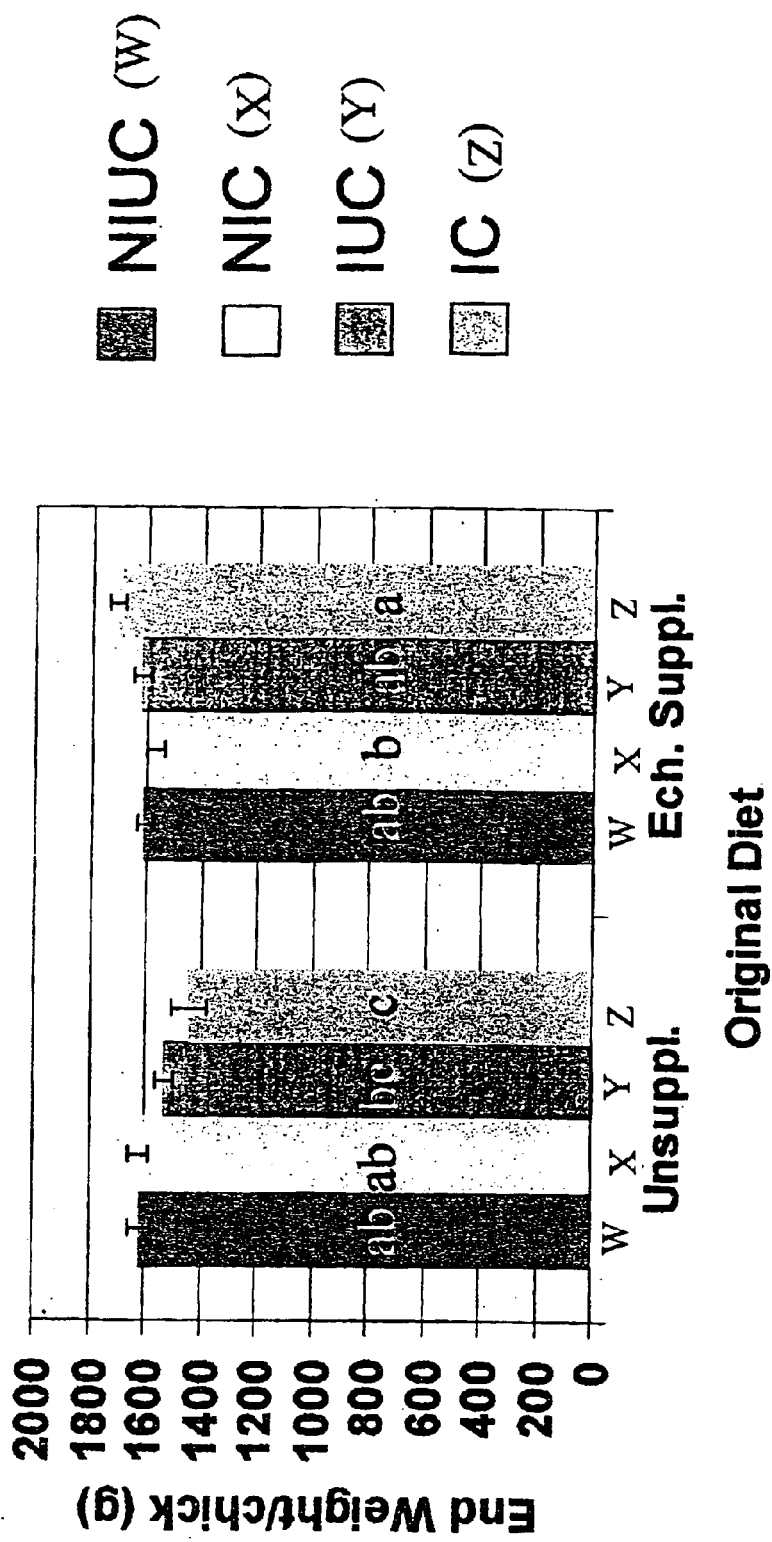
FIG. 4 shows the effect of challenge with coccidia on body weight at 6 days PI. NIUC=nonimmunized, unchallenged; NIC=nonimmunized, challenged; IUC=immunized, unchallenged; IC=immunized, challenged. $^{ab}$Values are means±SEM. Columns with no common letter have significantly different values (p>0.05).
Figure 5:
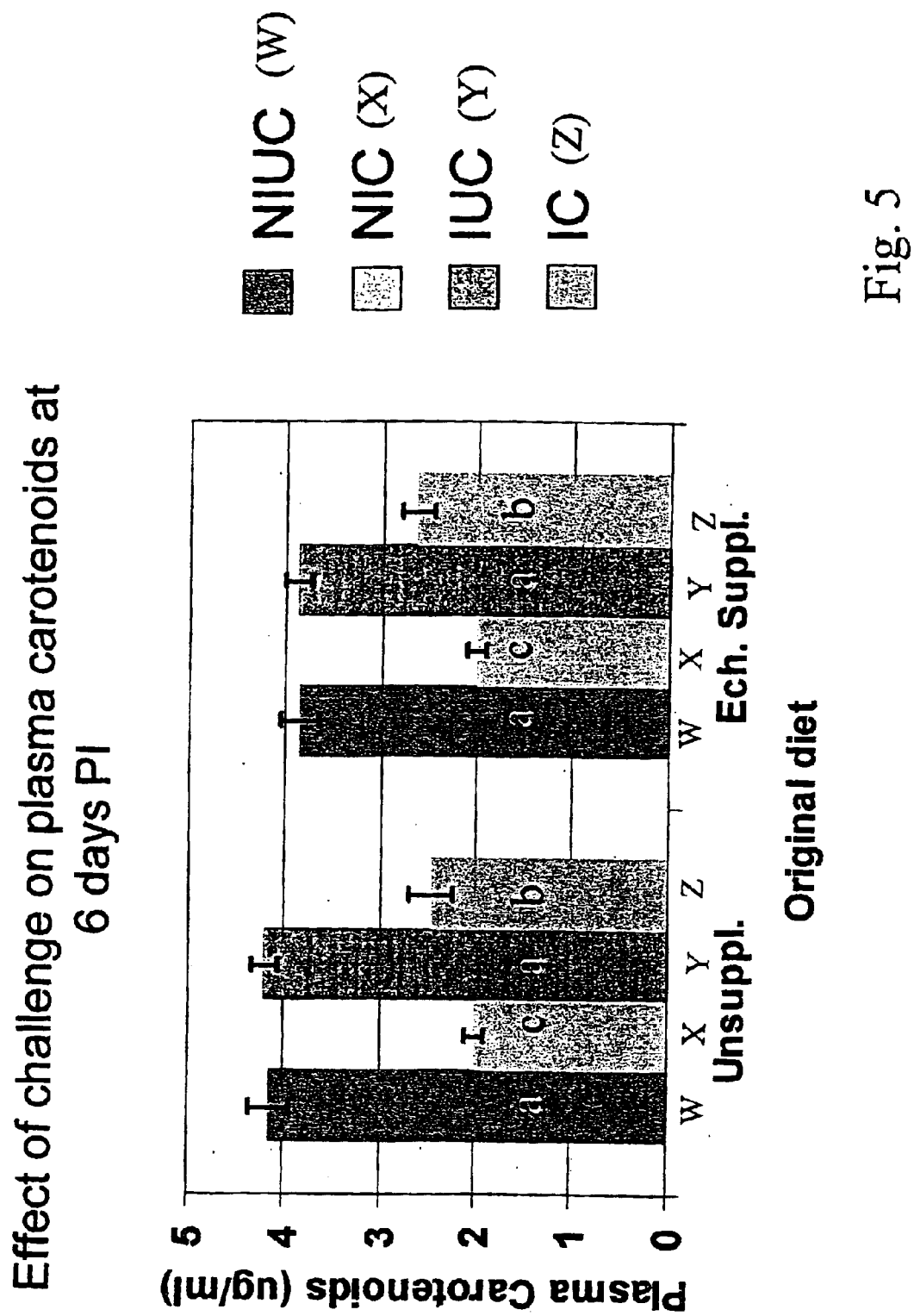
FIG. 5 shows the effect of challenge on plasma carotenoids at 6 days PI. NIUC=nonimmunized, unchallenged; NIC=nonimmunized, challenged; IUC=immunized, unchallenged; IC=immunized, challenged. [a,b]Values are means±SEM. Columns with no common letter have significantly different values ($p>0.05$).
Figure 6:
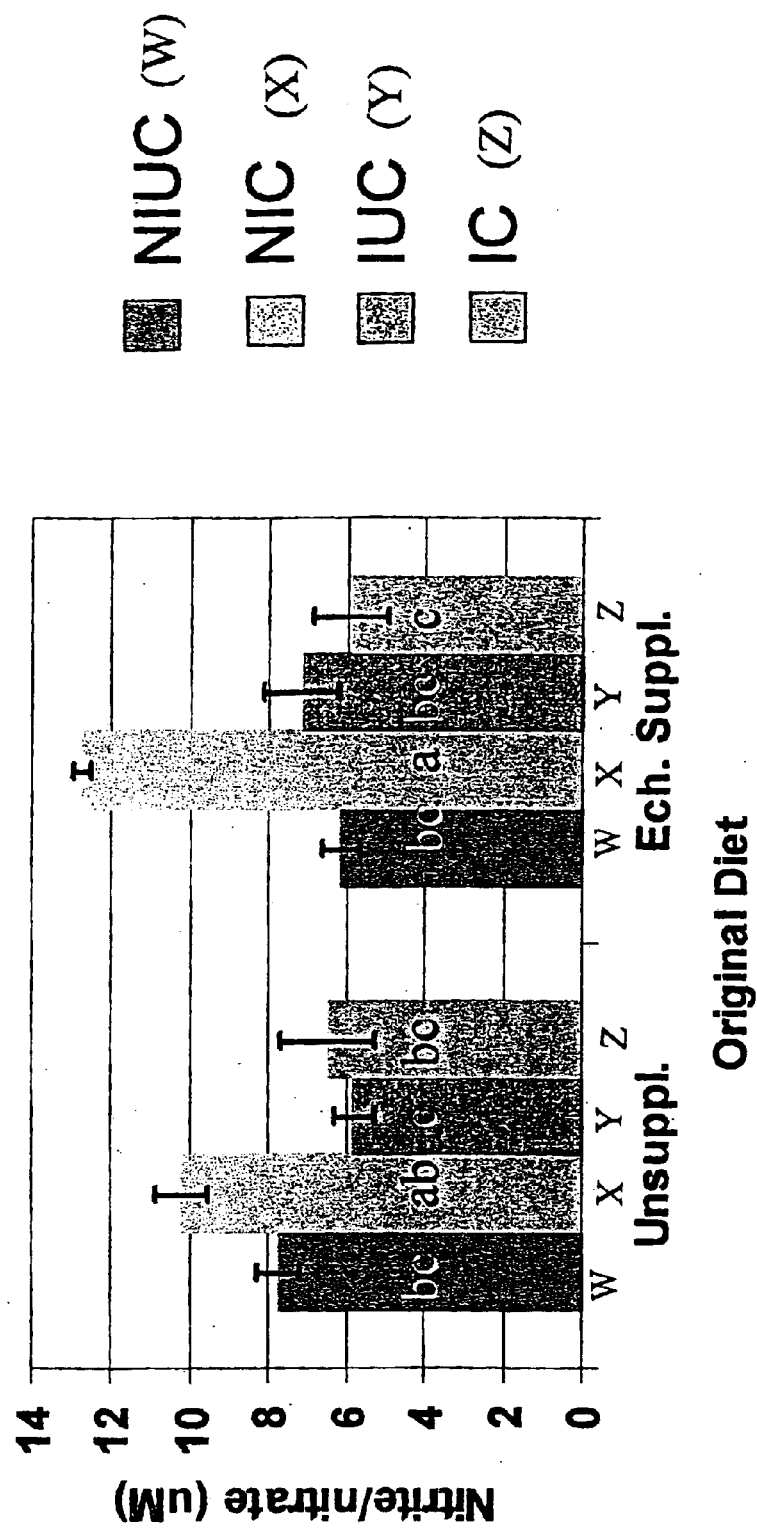
FIG. 6 shows the effect of challenge on plasma nitrite/nitrate at 6 days PI. NIUC=nonimmunized, unchallenged; NIC=nonimmunized, challenged; IUC=immunized, unchallenged; IC=immunized, challenged. [a,b]Values are means±SEM. Columns with no common letter have significantly different values ($p>0.05$).

| Treatment | Diet | Upper | Middle | Ceca | Total Score |
|---|---|---|---|---|---|
| Un-immunized | 0 | 2.8 ± 0.2a | 0.9 ± 0.1a | 0.2 ± 0.2ab | 3.9 ± 0.3a |
| | Echinacea | 2.3 ± 0.2a | 0.7 ± 0.2a | 0.6 ± 0.1a | 3.6 ± 0.2a |
| Immunized | 0 | 1.8 ± 0.4b | 0.1 ± 0.1b | 0.6 ± 0.2a | 2.5 ± 0.3b |
| | Echinacea | 0.7 ± 0.2c | 0b | 0.1 ± 0.1a | 0.9 ± 0.2c | a–cValues are means ± SEM. Within columns, means with no common superscript are significantly different (p > 0.05)

plasma carotenoids (2.0 μg/ml compared to 4.0 μg/ml for unchallenged controls) in unimmunized chicks. Immunization partially reversed this effect (2.5 μg/ml) (FIG. 4). Challenge infection significantly increased plasma $NO_2^- + NO_3^-$ in unimmunized chicks (11.5 μM compared to unchallenged, 6.7 μM). Immunization abrogated this increase (6.2 μM) (FIG. 5). Echinacea supplementation did not significantly affect plasma levels of carotenoids or $NO_2^- + NO_3^-$ within immunization or challenge treatments.

The experiment demonstrated that combined live vaccination and feed supplementation with 0.1% or 0.5% Echinacea during the first two weeks of life provided significant weight gain advantage compared to live vaccination alone. This advantage persisted through two weeks of Echinacea withdrawal and challenge infection. Echinacea supplementation also significantly lowered total lesion scores but did not modify effects of vaccination and challenge on plasma carotenoids or $NO_2^- + NO_3^-$. The mode of action of Echinacea is unknown, however, it is has been reported to contain polyglycan constituents that nonspecifically stimulate phagocytosis and can inhibit growth of Candida albicans and Listeria monocytogenes in mice (Roesler et al., supra). The results of this experiment suggest that Echinacea dietary supplements are useful adjuvants for live vaccines, and may provide protective immunostimulation in the presence of natural populations of coccidia in litter.

The following example is intended only to further illustrate the invention and is not intended to limit the scope of the invention as defined by the claims.

EXAMPLE

Male processed broilers were obtained at one day of age from a commercial hatchery. Chicks were raised in Brower brooders for two weeks. Corrugated paper was used to line the floor of the brooders to allow recycling of oocysts from the live vaccine. Lighting was continuous, and chicks were allowed unlimited access to feed and water. After two weeks, chicks were placed, five per cage, in suspended wire cages in rooms held at about 28° C., with constant lighting and unlimited access to feed and water.

The chicks were immunized with Immucox® (Vetech Laboratories, Ltd., Rockwood, Ontario, Canada). The vaccine is a live vaccine composed of a proprietary mixture of a small number of live oocysts of four coccidia species: E. acervulina, E. tenella, E. maxima and E. necatrix. It was given orally at half strength for vaccination and a 1000× for challenge infection.

The chicks were fed a dried, ground (80 mesh) preparation of E. purpurea (Triarco Industries, Paterson, N.J.) mixed with broiler starter (BS) mash (4050, Southern States, supra) at 0.1% or 0.5% (w/w).

Day-old chicks were placed immediately on one of three diets: BS ration supplemented with 0, 0.1% or 0.5% ground Echinacea. Half of each diet group was immunized orally with half strength Immucox® resulting in six treatment groups of 20 chicks each. At two weeks, all chickens were placed on unsupplemented BS for a further two weeks, after which time each treatment group was divided into an unchallenged or challenged group (10 chicks/group) of equal mean weight. Chicks in challenged groups were each given a 1000× oral dose of the live vaccine. At six days post challenge, chickens were weighed, bled, killed and scored for lesions in upper and middle small intestine and ceca. Plasma samples were analyzed for carotenoids and nitrite/nitrate.

All references cited hereinabove are herein incorporated by reference.

What is claimed is:

1. A method for protecting poultry against coccidiosis, said method comprising 1) inoculating chicks with an effective amount of an anticoccidial vaccine and 2) providing a dietary regimen composition comprising a mixture of A) poultry feed and B) an Echinacea preparation in an amount effective for enhancing an immune response to said vaccine.

2. The method of claim 1, wherein said inoculation and said Echinacea supplementation are carried out simultaneously.

3. The method of claim 1, wherein said inoculation and said Echinacea supplementation are begun on day-old chicks.

4. The method of claim 1, wherein said Echinacea supplement is about 0.1% (w/w) to about 0.5% (w/w) of said dietary composition.

5. The method of claim 1, wherein said Echinacea supplement is removed from said dietary regimen after two weeks.

6. The method of claim 1, wherein said Echinacea supplement is Echinacea purpurea.

* * * * *